United States Patent

Rand

(10) Patent No.: US 7,467,629 B2
(45) Date of Patent: Dec. 23, 2008

(54) MEDICAMENT DISPENSER WITH MAGNETO-RHEOLOGICAL FLUID ACTUATOR

(75) Inventor: Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 803 days.

(21) Appl. No.: 10/498,785

(22) PCT Filed: Dec. 18, 2002

(86) PCT No.: PCT/EP02/14475

§ 371 (c)(1), (2), (4) Date: Jun. 16, 2004

(87) PCT Pub. No.: WO03/051438

PCT Pub. Date: Jun. 26, 2003

(65) Prior Publication Data

US 2005/0066961 A1  Mar. 31, 2005

(30) Foreign Application Priority Data

Dec. 19, 2001  (GB)  ................. 0130284.3

(51) Int. Cl.
*A61M 11/00*  (2006.01)
(52) U.S. Cl. .................. 128/200.14; 222/334
(58) Field of Classification Search ............ 128/200.14, 128/200.13, 204.18–204.22; 222/323, 334, 222/389; 252/62.51 R
See application file for complete search history.

(56) References Cited

U.S. PATENT DOCUMENTS

| | | | |
|---|---|---|---|
| 4,940,966 A | 7/1990 | Pettigrew et al. | |
| 5,397,028 A | 3/1995 | Jesadanont | |
| 5,772,085 A | 6/1998 | Bryant et al. | |
| 5,875,938 A | 3/1999 | Graf et al. | |
| 5,985,168 A | 11/1999 | Phule | |
| 6,299,031 B1 * | 10/2001 | Cavallaro et al. | 222/334 |
| 2005/0022806 A1 * | 2/2005 | Beaumont et al. | 128/200.14 |

FOREIGN PATENT DOCUMENTS

| | | |
|---|---|---|
| EP | 0 870 699 A2 | 10/1998 |
| EP | 1 146 259 A | 10/2001 |
| WO | 92 12402 A1 | 7/1992 |
| WO | 96 31790 A1 | 10/1996 |
| WO | 99 36334 A1 | 7/1999 |
| WO | 99 58874 A | 11/1999 |
| WO | 01/24690 A2 | 4/2001 |
| WO | 01 26020 A1 | 4/2001 |
| WO | 01 26021 A1 | 4/2001 |
| WO | 01 85245 A | 11/2001 |
| WO | 02 100469 A | 12/2002 |

* cited by examiner

*Primary Examiner*—Steven O Douglas
(74) *Attorney, Agent, or Firm*—Robert J. Smith

(57) ABSTRACT

A medicament dispenser that includes a body, a medicament container, a source of magnetic radiation, and actuation means that includes a magneto-rheological fluid is described.

14 Claims, 2 Drawing Sheets

MEDICAMENT DISPENSER WITH MAGNETO-RHEOLOGICAL FLUID ACTUATOR

Figure 1A:
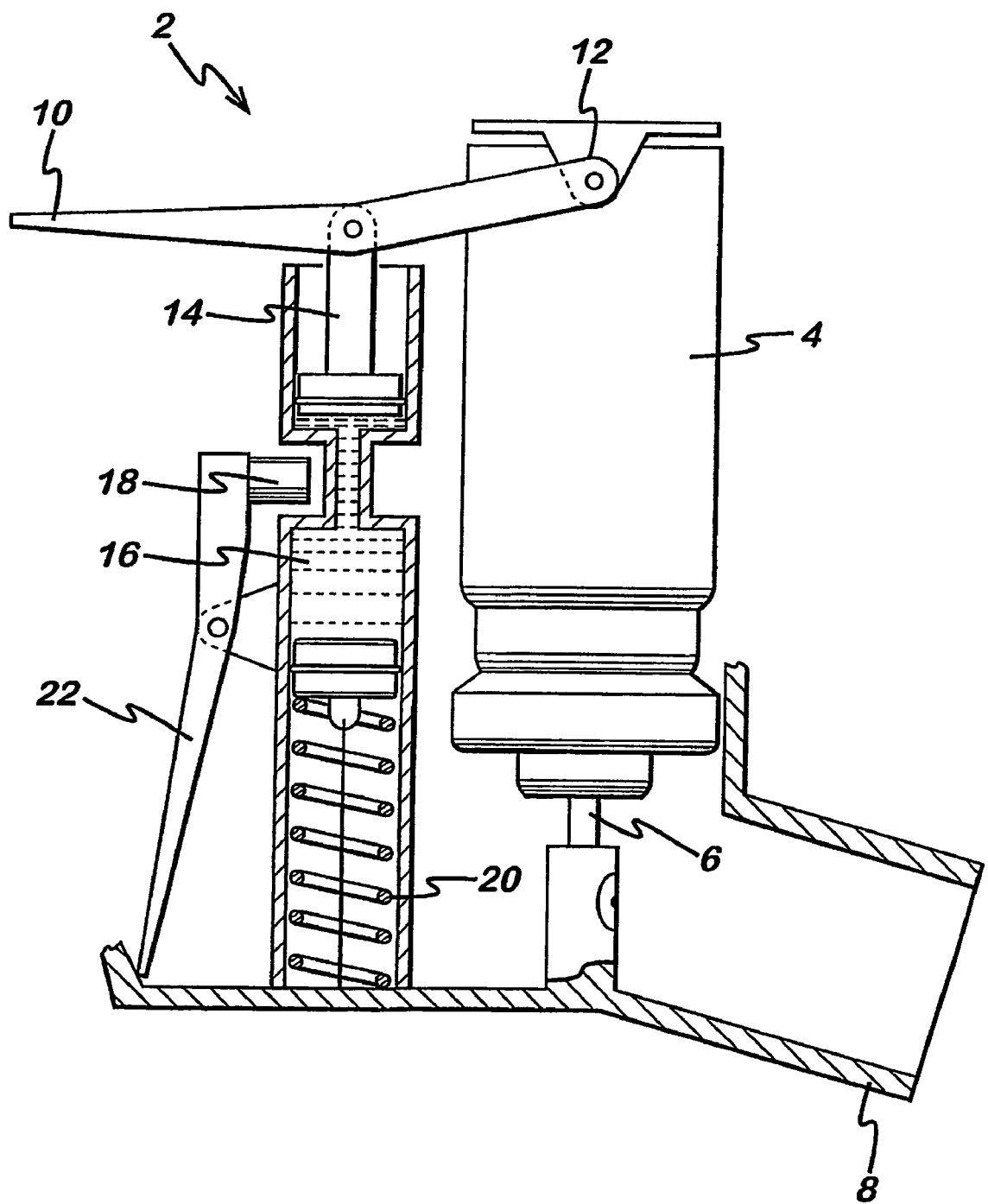

This application is filed pursuant to 35 U.S.C. § 371 as a United States National Phase Application of International Patent Application Ser. No. PCT/EP02/14475 filed Dec. 18, 2002, which claims priority from Great Britain Application No. 0130284.3 filed in the United Kingdom on Dec. 19, 2001.

This invention relates to a medicament dispenser having actuating means comprising a magneto-rheological (MR) fluid. The dispenser is particularly suitable for use as an inhalation device.

It is well known to treat patients with medicaments contained in an aerosol, for example, in the treatment of respiratory disorders. It is also known to use for such treatment, medicaments which are contained in an aerosol and are administered to a patient by means of an inhalation device comprising a tubular housing or sleeve in which the aerosol container is located and an outlet tube leading out of the tubular housing. Such inhalation devices are generally referred to as metered dose inhalers (MDIs). The aerosol containers used in such inhalation devices are designed to deliver a predetermined dose of medicament upon each actuation by means of an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example a nozzle or mouthpiece. When used for dispensing medicaments, for example in bronchodilation therapy, the patient then holds the housing in a more or less upright condition and the mouthpiece or nozzle of the inhalation device is placed in the mouth or nose of the patient. The aerosol container is pressed towards the support to dispense a dose of medicament from the container which is then inhaled by the patient.

It is also known to use dry powder inhalation devices for the delivery of inhalable medicament. In one aspect, such dispensers comprise pre-metered doses of powdered medicament, for example in capsules or blisters. In another aspect, such dispensers comprise a reservoir of powdered medicament from which doses are metered prior to or concurrent with the delivery process. In either case, the device may be designed for passive release of medicament, where the medicament is simply made available at a delivery position for aerosolisation in response to the inhalation of the patient. Alternatively, an active release mechanism may be used whereby a 'puff' of compressed gas or air is provided to the delivery position to assist in aerosolisation of the powder prior to or concurrent with the inhalation of the patient. Such devices are generally called active release dry powder inhalers (active DPIs). The source of the compressed gas or air is generally an aerosol container.

It is also well known to use syringes for the delivery of injectable medicament to a patient. Traditional syringes rely on puncturing of the patient's skin by a hollow needle through which the injectable medicament (in solution or suspension form) is delivered to the muscle or tissue of the patient. Recently developed needleless systems for the delivery of injectables employ high velocity injection of particle formulated drugs or vaccine through the skin and into any physically accessible tissue. Other needleless systems employ similar high velocity injection of drug or vaccine coated onto a suitable carrier particle. Such needleless systems may be configured to include a source of compressed air or gas, which on release provides energy to propel the medicament particles for injection into the skin.

It may be understood that effective delivery of medicament to the patient using an inhalation device such as an MDI or active DPI as described above is to an extent dependent on the patient's ability to manually actuate the device (e.g. firing of the aerosol) and to co-ordinate the actuation thereof with the taking of a sufficiently strong inward breath. For some patients, particularly young children, the elderly and the arthritic, manual actuation of the device can present difficulties. Other patients find it difficult to co-ordinate the taking of a reliable inward breath with actuation of the device. Both of these sets of patients run the risk that they do not receive the appropriate dose of medicament.

It may also be understood that effective delivery of medicament to the patient using a syringe or needleless injection system as described above also requires care and dexterity.

U.S. Pat. No. 5,397,028 discloses an automatic dispenser for spraying a liquid. The device uses an electromagnet to move a magnetic frame downwards against an inverted bottle of liquid in order to dispense the liquid.

Similarly, U.S. Pat. No. 5,875,938 discloses a discharge device wherein permanent magnets are provided for controlling a piston unit and valves and hence dispensing of the contents thereof.

The Applicants have now developed a medicament dispenser which inter alia, may not require manual actuation by the patient. The dispenser uses magneto-rheological (MR) fluid suspension technology to actuate one or more mechanical and/or electromechanical mechanisms of the dispenser.

MR fluids are essentially suspensions or dispersions of ultra-fine micron-sized (~0.05 to 10 micrometer) magnetically soft, multidomain particles in oil. Under normal conditions, an MR fluid is a free-flowing viscous liquid. However, on exposure to a magnetic field, the suspension is transformed into a near solid state in milliseconds. The change in state can appear as a very large change in effective viscoscity (by as much as $10^6$).

Moreover, removal of the magnetic field reverses the state transition in the same ime scale. The extent of the change in state of an MR suspension is proportional to the magnetic field strength. Such suspensions can develop a yield strength and behave as Bingham solids.

U.S. Pat. No. 5,985,168 discloses the technology surrounding MR fluids. MR suspensions have a number of advantages over electro-rheological (ER) fluids in that they are more stable, non-corroding and have a higher yield stress.

Accordingly, in one aspect the invention provides a medicament dispenser having a body, a medicament container, a source of magnetic radiation and actuating means, wherein said actuating means comprises an MR fluid.

The MR fluid and thus the actuating means is responsive to the application and/or withdrawal of the magnetic field created by the source of magnetic radiation.

Preferably, the dispenser further comprises a resilient biasing member to bias the flow of the MR fluid in the absence of magnetic radiation.

As used herein, the term actuating means refers to means associated with the dispenser for actuating a mechanical and/or electromechanical mechanism of the dispenser. Accordingly, the actuating means may take the form of a valve, and/or a switch, and/or a lever, and/or a pump (e.g. an aqueous pump), and/or a plunger (e.g. as in an automated syringe).

The actuating means may actuate dose-liberating means such as a valve, and/or dose-metering means (e.g. a dose-metering valve in an aerosol container of medicament), and/ or means to aerosolize a dose of dry powder medicament, and/or means to uncover or open a sealed container/capsule of pre-metered dry powder medicament, and/or means to transport a metered amount of medicament from a rest position to a delivery position, and/or means to pump a dose of medicament for receipt by a patient (e.g. an aqueous pump), and/or a plunger (e.g. as in an automated syringe).

Suitably, the valve is a slide valve. Other valve systems include, but are not limited to, poppet valve systems, wedge gate valve systems, double-disc gate valve systems, globe and angle valve systems, swing check valve systems, end cock valve systems, and other like valve systems. The valve design is typically a function of providing a predetermined dosage or amount of the medicament contained within the container to a user.

Where the medicament container is a pressurized aerosol container, the valve typically comprises a valve body having an inlet port through which a medicament aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 µl, such as 25 µl, 50 µl or 63 µl. Suitably, the valve body defines a metering chamber for metering an amount of medicament formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of medicament formulation into the metering chamber.

The valve may also comprise a 'free flow aerosol valve' having a chamber and a valve stem extending into the chamber and movable relative to the chamber between dispensing and non-dispensing positions. The valve stem has a configuration and the chamber has an internal configuration such that a metered volume is defined therebetween and such that during movement between is non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation. A valve of this type is described in U.S. Pat. No. 5,772,085.

The valve may also have a structure and action similar to those aerosol valves described in European Patent Application No. EP-A-870,699 and PCT Patent Application No. WO99/36334.

The dose-metering means may comprise a volume and/or a time and/or a surface-area regulated mechanism.

In one embodiment the dose-metering means may comprise a valve as described supra (for example, a linear or rotary valve) and/or a piston and/or a load cell and/or a plunger.

Preferably, the dose-metering means comprises at least one metering chamber.

On actuation of the dose-metering means, the or each metering chamber may move into fluid communication with the reservoir.

Alternatively, or in addition, the dose-metering means and the reservoir may be relatively rotatable with respect to each other about a common central axis.

In one embodiment the or each metering chamber is adapted to be in fluid communication selectively with the reservoir or with the patient.

The or each metering chamber may have a variable volume.

The or each metering chamber may have a fixed volume which metering volume is variable by insertion of a plunger or piston.

The or each metering chamber may be formed from expandable material.

The or each metering chamber may have a telescopic or concertina arrangement.

In one embodiment, there may be a gas permeable dry powder retaining means below the or each metering chamber. The retaining means may be made from a gas-permeable filter, a mesh screen, a porous material or a perforated chamber element.

The aerosolization means may comprise a container of compressed gas (e.g. an inert gas or air), or a liquefied propellant under pressure.

The aerosolization means may comprise means to propel pressurised gas through a metered dose. The gas-propelling means may provide at least one pulse of gas on actuation. The gas-propelling means may provide one pulse of gas for each dose dispensed. The gas may be air or an inert gas.

In one embodiment, the medicament dispenser is in the form of an active dry powder inhaler in which a "puff" of compressed air or gas (e.g. helium) is delivered from the aerosolisation means, such as an aerosol container, to aerosolize a dose of released dry powder medicament.

In another embodiment, the medicament dispenser is in the form of a needleless injection system in which compressed air or gas (e.g. helium) is delivered at high velocity from the aerosol container to propel a dose of dry powder medicament for injection into the skin.

Thus, suitably the aerosol container, which as used herein refers to any suitable container for comprising liquefied gas under pressure, comprises a compressed air or gas (e.g. helium).

In another aspect, the medicament container may be arranged for rupture in response to firing of the aerosolisation means.

In one embodiment, the medicament is pre-metered prior to actuation of the dispenser by the patient, for example, the medicament is pre-metered in capsules, strip or tape form.

The container-opening means may liberate the medicament from the medicament container for receipt by a patient.

The aerosolization means may liberate a pre-metered dose of medicament for receipt by a patient.

The transport means may comprise a perforated strip and claw advancement mechanism and/or a ratchet wheel and a driving pawl advancement mechanism.

The pump may comprise a pump mechanism such as might be found in a dispenser for dispensing liquid or solution (e.g. aqueous solution) form medicament. The pump may deliver the medicament directly to the patient (e.g. as a nasal spray) or the pump may deliver the medicament to an intermediate position at which further energy is supplied thereto to further propel, aerosolize or otherwise direct the medicament dose to the patient.

The dose-liberating means may comprise multiple plungers and multiple syringe chambers. The syringe contents may for example, be liquid, solutions, suspensions, particulates or in freeze-dried form. A retract or reset mechanism is typically provided for the plunger.

Traditional syringes rely on puncturing of the patient's skin by a hollow needle through which the injectable medicament (in solution or suspension form) is delivered to the muscle or tissue of the patient. Recently developed neeedless systems for the delivery of injectables employ high velocity injection of particle formulated drugs or vaccine through the skin and into any physically accessible tissue. Other needleless systems employ similar high velocity injection of drug or vaccine coated onto a suitable carrier.

A reset mechanism may be provided for resetting the actuating means after actuation thereof. The reset mechanism may for example, comprise a spring, motor, mechanical arrangement or an MR fluid.

Preferably, the actuating means is responsive to a patient-actuable mechanism.

In one aspect, said mechanism comprises a button, switch or lever arrangement.

In another aspect, the medicament dispenser is in the form of an inhaler for the delivery of inhalable medicament. Preferably, the actuating means is responsive to a patient-actuable mechanism comprising a sensor which senses the breath of a patient. The actuating means may be responsive to the detection of the inward breath of a patient. Alternatively, the actuating means may be responsive to a mechanism coupled to any point in the breathing pattern of the patient, such as the end of the outward breath.

In one aspect, the sensor comprises a breath-movable element which is movable in response to the breath of a patient. Preferably, the breath-movable element is selected from the group consisting of a vane, a sail, a piston, a diaphragm and an impeller.

Movement of the breath-movable element may be detectable by any suitable technique for detecting movement. Suitable techniques include optical detectors, magnetic detectors or detectors using detection of capacitative effects.

Optical detectors may be used to detect movement of the breath-movable element by providing the element with a patterned outer surface, for example strips in a barcode type arrangement, and locating the optical detector so that it points towards the patterned surface. Movement of the breath-movable element alters the amount of the light source which reflects back onto the optical detector as the beam passes over the patterned surface. The strips may be arranged so that the direction of movement of the element can be detected.

Magnetic detectors may be used to detect the movement of breath-movable element by the use of a magnetic switch device. A reader is located on the dispenser and magnetic material embedded within the breath-movable element (or vice-versa). Movement of the breath-movable element results in a change of the magnetic field experienced by the reader. Alternatively, a Hall effect device can be used whereby a semiconductor measures the strength of the magnetic field of the magnetic material on the breath-movable element.

Detection of capacitative effects may be used to detect movement of the breath-movable element by adding a conductive part to the element and also to a second fixed part of the dispenser. Movement of the breath-movable element results in a change in capacitance which can be measured.

In another aspect, the sensor comprises a pressure sensor for sensing the pressure profile associated with the breath of a patient. A pressure transducer is an example of a suitable pressure sensor.

In another aspect, the sensor comprises an airflow sensor for sensing the airflow profile associated with the breath of a patient.

In another aspect, the sensor comprises a temperature sensor for sensing the temperature profile associated with the breath of a patient.

In another aspect, the sensor comprises a moisture sensor for sensing the moisture profile associated with the breath of a patient.

In another aspect, the sensor comprises a gas sensor for sensing the oxygen or carbon dioxide profile associated with the breath of a patient. The chemical profile of the inhaled and exhaled part of the breath cycle varies and this further may be used as a measurement tool.

Suitably, the breath data includes breath cycle data, $FEV_1$ and/or peak flow data.

Preferably the medicament dispenser comprises an actuation or dose counter for counting the number of actuations of the actuating means. The actuation or dose counter may be mechanical or electronic. More preferably the actuation or dose counter is independent of the actuating means so that counting will occur even if the dispenser is actuated by means other than the actuating means, e.g. manually.

The source of magnetic radiation may be a permanent magnet or an electromagnet.

Preferably, the medicament dispenser additionally comprises an electrical energy source for providing electric current, or for providing an electric field, or for powering an electromagnet to provide a magnetic field. In one aspect, the electrical energy source comprises a voltaic cell or battery of voltaic cells which may be rechargeable. In another aspect, the electrical energy source comprises a photovoltaic cell or battery of photovoltaic cells. In a further aspect, the electrical energy source comprises a converter for converting mechanical energy into electrical energy. In a further aspect, the electrical energy source comprises a capacitor for local storage of charge. Suitable capacitors comprise those known as 'super capacitors' with a high capacitance to size ratio, such as those consisting of solid electrodes and liquid electrolyte.

Any known systems for power management and conservation may be employed with the electrical energy source to manage and/or conserve the power output thereof.

Energy may be conserved by a variety of means to enable the device to operate for longer on a given source of energy, such as a battery. Energy conservation or saving methods have additional advantages in terms of reducing the size requirements of the power source (e.g. battery) and thus the weight and portability of the inhalation device.

A variety of energy saving methods are available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers.

Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Any electrical circuit may incorporate voltage amplification means for generating a higher voltage than that supplied by the voltaic cell or battery of voltaic cells, for example a step-up or inverting switching circuit or a dc-dc converter incorporating an oscillator, transformer and rectifier.

The electrical circuit may incorporate one or more energy storage components such as capacitors or inductors in order to supply a high enough instantaneous current to raise the temperature of any strips or wires at the required rate to the required temperature, if required.

The input to the electrical circuit may be connected to the electrical energy source by means of a mechanical, electromechanical or electronic switching component.

The output of the electrical circuit may be connected to any strips or wires or to an electromagnet by means of a mechanical, electromechanical or electronic switching component or by a component allowing the output current to be controlled in a linear or digital (e.g. pulse width modulated) manner.

Any strip or wire components or an electromagnet may be powered from the battery using a switching component without additional power supply circuitry.

Suitably, the medicament dispenser additionally comprises a controller for controlling the amount of electrical current flow through a component of the dispenser, e.g. an electromagnet.

Suitably, the medicament dispenser additionally comprises a timer for controlling the duration of electrical current flow through a component of the dispenser, e.g. an electromagnet.

Suitably, the medicament dispenser additionally comprises a local electrical source such as a capacitor or inductor.

The additional energy source may be mechanically generated, for example, the energy source may comprise a biasable resilient member e.g. a spring. Alternatively, the energy source may comprise a source of compressed fluid, preferably compressed gas. The energy source may comprise a chemical energy source or a physically explosive energy source.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system comprises an electronic control system for controlling the supply of energy to a component of the dispenser, e.g. an electromagnet. Thus, in aspects the control system may regulate flow of electrical current to an electromagnet source associated therewith.

The control system may form part of a larger electronic data management system capable of receiving inputs from other electronic components. In particular, inputs may be received from any sensor to enable actuation of the actuating means in response to sensor, particularly breath sensor input.

The control system may be arranged to accomplish any suitable control of actuation of the actuating means including varying the amount of energy supplied to a component of the dispenser, e.g. an electromagnet, the rate of energy supplied thereto, pulsing patterns of energy supply to the electromagnet, and more complex control patterns.

Suitably, the electronic data management system is arranged to be responsive to or activated by the voice of a user. Thus, for example the system may be switched on or off in response to a voice command.

The electronic data management system may be integral with the body. Alternatively, the electronic data management system forms part of a base unit which is reversibly associable with the body.

Suitably, the medicament dispenser additionally comprises a data input system for user input of data to the electronic data management system. Preferably, the data input system comprises a man machine interface (MMI) preferably selected from a keypad, voice or noise recognition interface, graphical user interface (GUI) or biometrics interface.

Suitably, the system additionally comprises a visual display unit for display of data from the electronic data management system to the user. The display may for example, comprise a screen such as an LED or LCD screen. More preferably the visual display unit is associable with the housing. More basic display units are envisaged also including those in which a light or pattern of lights is employed to act as a signal to the patient.

The electronic data management system may further comprise a voice synthesiser for verbal communication of data, instructions and feedback to a user.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement medicament containers. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hard-wired link, an infra red link or any other suitable wireless communications link.

Suitably, the medicament dispenser additionally comprises an actuation detector for detecting actuation of the actuating means wherein said actuation detector transmits actuation data to the electronic data management system.

The medicament dispenser may additionally comprise a safety mechanism to prevent unintended multiple actuations of the actuating means. The patient is thereby protected from inadvertently receiving multiple doses of medicament in a situation where they take a number of short rapid breaths. More preferably, the safety mechanism imposes a time delay between successive actuations of the actuating means. The time delay is typically of the order of from three to thirty seconds.

Suitably, the medicament dispenser additionally comprises a release detector for detecting release of medicament from the medicament container, wherein said release detector transmits release data to the electronic data management system.

Suitably, the medicament dispenser additionally comprises a shake detector for detecting shaking of the medicament container (e.g. prior to actuation of the trigger means), wherein said shake detector transmits shake data to the electronic data management system.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from the dispenser. In one aspect, the selector is manually operable. In another aspect, the selector is operable in response to a signal from the transmitter on the electronic data management system.

Suitably, the medicament dispenser comprises in association with a body or housing thereof, a first transceiver for transmitting and receiving data and in association with the medicament container, a second transceiver for transmitting and receiving data, wherein data is transferable in two-way fashion from the first transceiver to the second transceiver. The data is preferably in digital form and suitable for transfer by electronic or optical means. A medicament dispenser of this general type is described in pending UK Patent Application No. 0020538.5.

The body or housing of the medicament dispenser is typically shaped to define a cavity within which the medicament container is receivable. The body and/or medicament container may be further shaped with any manner of grooves, indentations or other shaping or surface details to define a 'lock and key' relationship between the body and the container. Colour guides, arrows and any other surface markings may also be employed.

One advantage of embodiments of this type is the ability to store many types of information in different parts of the memory structure of the transceivers. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

On loading or reloading the dispenser with a medicament container (such as an aerosol canister or dry powder cassette) the second transceiver may, for example, read the unique serial number, batch code and expiry date of the medicament and any other information on the second transceiver. In this way the nature and concentration of the medicament, together with the number of doses used or remaining within the container, may be determined. This information can be displayed to the patient on a visual display unit. Other information, such as the number of times the dispenser has been reloaded with a medicament container, may also be displayed.

Similarly, should the container be removed from the housing before the supply of medicament is exhausted, the same data can be read from the second transceiver and the number of doses remaining or used determined. Other information, such as the date and time of administration of the drug, or environmental exposure data such as the minimum/maximum temperatures or levels of humidity the medicament container has been exposed to, may also be read and displayed to the user.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the device. Or alternatively, data may be stored in a database memory of the electronic data management system and periodically downloaded to any transceiver. In either case, a history of the usage of the device may be built up in the memory of a transceiver.

In one embodiment herein, a history of the usage of the medicament dispenser is transferred to the second transceiver on the aerosol container. When the medicament container is exhausted it is exchanged by the patient for a new refill container. At the point of exchange, which will typically occur at the pharmacy, data may be transferred from the exhausted container to the refill and vice-versa. Additionally, usage history data may be read from the refill and transferred to a healthcare data management system for example comprising a network computer system under the control of a healthcare data manager.

Methods are envisaged herein whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or one dispensing) to or from any transceiver can be arranged to be readily achievable by the use of a reader which is remote from the medical dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween.

Preferably, data is transferable wirelessly between the first and second transceiver.

Suitably, the first transceiver is an active transceiver and the second transceiver is a passive transceiver. The term active is used to mean directly powered and the term passive is used to mean indirectly powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver.

Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or housing of the medicament dispenser or the medicament container.

In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is mouldable or weldable to the medicament container or housing. Suitably, the carrier encases the tag. More preferably, the carrier forms a hermetic seal for the tag.

In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 KHz to 2.5 GHz. Preferred operating frequencies are selected from 125 KHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system. Dispensers employing such communicators are described in pending PCT Applications No.s PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto. More preferably, information from the user-specific network address can be made available to the remote information source.

In one aspect, the remote information source is a medicament prescriber, for example a doctor's practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests which have been remotely pre-authorised by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

In a further aspect, the remote information source is a computer software download site from which software may be downloaded for use in the electronic data management system. Embodiments are envisaged in which such software downloads are employed to upgrade or modify any existing software employed by the electronic data management system.

Suitably, the medicament dispenser additionally comprises a geographic positioning system such as a global positioning system or a system which relies on the use of multiple communications signals and a triangulation algorithm.

In another embodiment, the dispenser additionally comprises climate control means.

The climate control means may comprise means to (i) reduce moisture increase in the dispenser; and/or (ii) maintain ambient temperature; and/or (iii) dry the meter prior to actuation of the dispenser.

The climate control means may comprise a desiccant and/or a heater.

The climate control means may comprise a temperature and/or a moisture sensor. The dispenser of the invention is suitable for dispensing medicament, particularly for the treatment of respiratory disorders such as asthma and chronic obstructive pulmonary disease (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate). A particularly preferred combination comprises salmeterol xinafoate salt and fluticasone propionate.

Preferred medicaments are selected from albuterol, salmeterol, fluticasone propionate and beclomethasone dipropionate and salts or solvates thereof, e.g., the sulphate of albuterol and the xinafoate of salmeterol, and any mixtures thereof. Alternatively, the dispenser may be employed for dispensing vaccine.

The medicament container may comprise medicament in dry powder form. Typically, a dry powder medicament includes a pharmaceutical excipient in dry powder form.

In one embodiment, the density of the dry powder medicament particles is reduced relative to standard dry powder medicament.

In another embodiment, the dry powder medicament particles are aerodynamically shaped to improve medicament delivery to the patient.

In another embodiment, the medicament container may comprise medicament in solution or suspension form.

The medicament container may comprise a suspension of a medicament in a propellant, for example, liquefied HFA134a, HFA-227, helium or carbon dioxide.

Alternatively, the medicament container may comprise a solution of a medicament in a solvent.

Preferably, the medicament dispenser additionally comprises a safety mechanism to prevent unintended multiple actuations of the dispenser.

The safety mechanism may impose a time delay between successive actuation of the dispenser.

Preferably, the medicament dispenser comprises a manual override enabling manual actuation of the dispenser. The manual override may be designed to cover all situations in which the actuating means does not actuate in the normal manner. These will include situations where actuation does not happen (e.g. due to power failure). Alternatively, this will include situations where actuation occurs, but reset of the actuating means fails to occur.

Preferably, the medicament dispenser comprises a child resistance feature to prevent undesirable actuation thereof by children.

In another aspect, the invention provides an actuator for use in a medicament dispenser as described hereinabove.

In a further aspect, the invention provides an actuator for a medicament container comprising a housing, within said housing, a container seat for receipt of the medicament container; on the housing or connecting therewith, a source of magnetic radiation and actuating means, wherein the actuating means comprises an MR fluid component.

The actuator herein may be configured to include, as relevant, any of the above described features of the medicament dispenser. In particular, the actuator may be configured to include an electronic data management system comprising control means for the actuation of the actuating means.

Suitably, the actuator additionally comprises an electronic control system for controlling the supply of energy to the source of magnetic radiation. Suitably, the electronic control system is capable of providing pulses of energy to the source of magnetic radiation.

Suitably, the electronic control system is capable of receiving inputs from electronic sensors locatable on the dispenser. Suitably, the actuator additionally comprises an electronic sensor selected from the group consisting of a breath sensor, a shake sensor, a temperature sensor, an infrared sensor and a patient ID sensor.

In a further aspect, the invention provides a valve for use in a medicament dispenser or actuator as defined supra, wherein the valve comprises a source of magnetic radiation and an MR fluid.

In a further aspect, the invention provides a medicament container for use in the dispenser and/or the actuator as described hereinabove.

According to a further aspect of the present invention there is provided a laboratory test apparatus comprising at least one actuator as described above and a mounting (e.g. a bench mounting) for the at least one actuator. The laboratory test apparatus is designed for use in testing the performance of the medicament dispenser in a laboratory environment. Often, plural actuators will be mounted on a single mounting to enable simultaneous testing thereof. The laboratory test apparatus will typically be connected to various sensors and recording devices for monitoring aspects of the performance of the medicament dispenser.

According to a further aspect of the present invention there is provided a kit of parts comprising a medicament dispenser as described above in the form of a cartridge; and a housing shaped for receipt of said cartridge.

According to a further aspect of the present invention there is provided a kit of parts comprising an actuator as described above and, receivable by said actuator, a medicament container.

In a preferred commercial embodiment herein, the actuator is arranged for receipt of a refill cartridge. Typically, the actuator is in the form of a relatively complex device, including for example an electronic data management system and the cartridge is in the form of a medicament refill therefor.

In another aspect the cartridge comprises a medicament dispenser having a voltaic cell as an electrical energy source and the housing is provided with a mouthpiece for patient inhalation therethrough and electronic information display apparatus for displaying information to the patient.

Figure 1B:
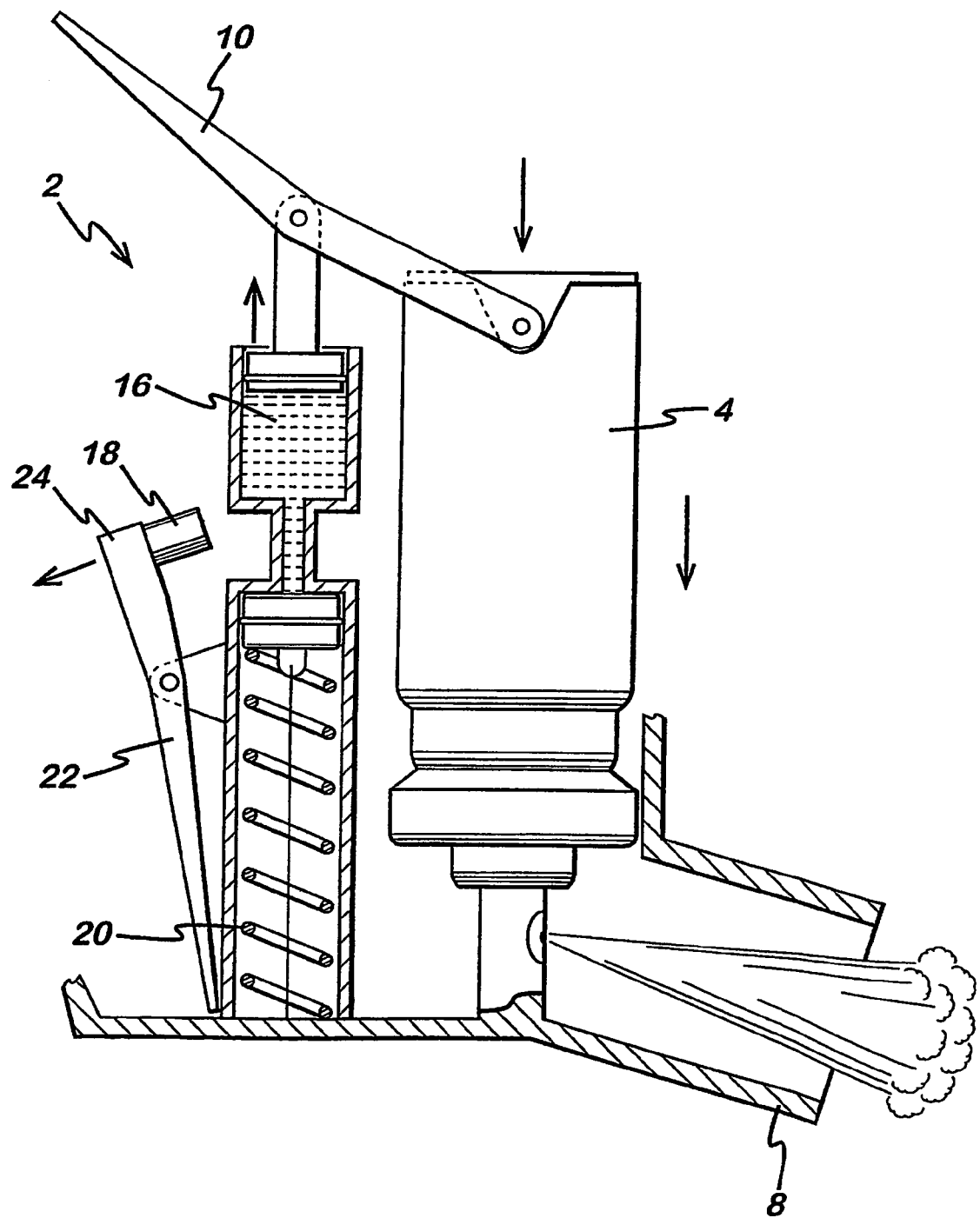

The invention will now be described further with reference to the accompanying figures in which:

FIG. 1a shows an inhaler in accordance with one embodiment of the invention in a rest position; and, FIG. 1b shows the inhaler of FIG. 1a in a firing position.

Referring now to the figures, FIGS. 1a and 1b schematically represent a breath operated metered dose inhaler 2. The inhaler comprises a canister 4 containing a suspension of medicament in a pressurised propellant such as p134a. The canister is linked at it base to a valve 6. Relative movement of the canister 4 with respect to the valve 6 results in a metered dose of medicament being dispensed to the patient. A mouthpiece 8 protrudes from the inhaler for passage of the medicament to the patient.

At rest (as shown in FIG. 1a) the canister 4 is retained in a non-dispensing position by a setting lever 10 pivotally mounted on the canister at position 12 and linked to a piston 14. The piston is locked in position by a plug 16 of MR fluid which is in a solidified state due to the action of a permanent magnet 18. A drive spring 20 is maintained in a compressed state underneath the plug 16. The spring 20 acts as an energy store for actuating the dispensing mechanism of the inhaler as described infra.

To fire the dispenser 2 and release a dose of medicament, the patient inhales and activates a breath sensor (the breath responsive vane of which is shown 22) which subsequently releases a trigger lever 24 linked to the permanent magnet 18. The magnet 18 is levered away from the MR plug 16 thus returning the MR plug to a liquid flowable state. The transformation of the MR fluid from a solid to a liquid now releases the spring 20, driving the fluid plug 16 and the piston 14 upwards and thus the canister 4 downwards with respect to the valve 6.

A reset means is not shown in the figures. The advantages of having a positive reset mechanism are numerous. In devices where there is no reset mechanism it is possible for the canister to stick in the firing position. This may effect the efficacy of further inhaler actuations as well as dosing efficacy and can result in medicament leakage. Furthermore, the longer the canister remains in the firing position, the increased likelihood of medicament deposition and/or increased medicament concentration in the lower parts of the canister. A positive reset mechanism is therefore technically advantageous in addition to increasing consumer confidence and ease of use of the device.

There may be either a separate reset button linked to the reset means or the reset means may be actuated after a predetermined time delay post firing of the dispenser. The reset mechanism may also comprise an MR fluid component.

It may be appreciated that any of the parts of the inhaler or actuator which contact the medicament suspension may be coated with materials such as fluoropolymer materials which reduce the tendency of medicament to adhere thereto. Any movable parts may also have coatings applied thereto which enhance their desired movement characteristics. Frictional coatings may therefore be applied to enhance frictional contact and lubricants used to reduce frictional contact as necessary.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

The invention claimed is:

1. A medicament dispenser comprising:
   a body,
   a medicament container for containing medicament in said dispenser for movement from a non-dispensing state, in which medicament is not dispensed from said container, to a dispensing state, in which medicament is dispensed from said container, and
   a magneto-rheological fluid actuator for moving said container from its non-dispensing state to its dispensing state, wherein said actuator comprises magneto-rheological fluid which is transformable from a solidified state to a liquid flowable state by a source of magnetic radiation, and wherein said actuator is adapted to move said container from its non-dispensing state to its dispensing state in response to said magneto-rheological fluid transforming from its solidified state to its liquid flowable state.

2. A medicament dispenser according to claim 1 further comprising a resilient biasing member to bias the flow of the magneto-rheological fluid in the absence of magnetic radiation to cause said actuator to move said container from its non-dispensing state to its dispensing state.

3. A medicament dispenser according to claim 1 wherein said actuator actuates a valve of said container.

4. A medicament dispenser according to claim 1, in the form of an inhaler for the delivery of inhalable medicament.

5. A medicament dispenser according to claim 4, wherein said actuator is responsive to a patient-actuable trigger comprising a sensor which senses the breath of a patient.

6. A medicament dispenser according to claim 5, wherein said sensor comprises a breath-movable element which is movable in response to the breath of a patient.

7. A medicament dispenser according to claim 6, wherein said breath-movable element is a vane.

8. A medicament dispenser according to claim 1 wherein said source of magnetic radiation is a permanent magnet or an electromagnet.

9. A medicament dispenser according to claim 1 wherein said medicament container contains medicament in solution or suspension form.

10. A medicament dispenser according to claim 9, wherein said medicament container contains a suspension of a medicament in a propellant.

11. A medicament dispenser according to claim 1 wherein said magnetic radiation source is adapted to selectively apply magnetic radiation to said magneto-rheological fluid, said magneto-rheological fluid adopting its solidified state in the presence of magnetic radiation from said magnetic radiation source and its liquid flowable state in the absence of magnetic radiation from said magnetic radiation source.

12. A medicament dispenser according to claim 1, wherein said magnetic radiation source is a permanent magnet which is mounted for movement from a first position, which causes said magneto-rheological fluid to adopt its solidified state, to a second position, which allows said magneto-rheological fluid to move to its liquid flowable state.

13. A medicament dispenser according to claim 1, wherein said medicament container is a canister.

14. A medicament dispenser comprising:
a mount for engaging a medicament container, the mount being movable between at least a first and a second position for moving the medicament container from a non-dispensing state to a dispensing state, respectively, and
a magneto-rheological fluid actuator being interconnected to the mount for moving the mount between the first and second positions, wherein said actuator comprises magneto-rheological fluid which is transformable from a solidified state to a liquid flowable state by a source of magnetic radiation, and wherein said actuator is adapted to move the mount from the first position to the second position in response to the magneto-rheological fluid transforming from its solidified state to its liquid flowable state.

* * * * *